United States Patent
Chen et al.

(10) Patent No.: US 10,211,410 B2
(45) Date of Patent: Feb. 19, 2019

(54) ORGANIC COMPOUND AND ELECTRONIC DEVICE USING SAME

(71) Applicant: Nichem Fine Technology Co., Ltd., Hsinchu County (TW)

(72) Inventors: Chien-Tien Chen, Hsinchu County (TW); Chi-Chung Chen, Hsinchu County (TW)

(73) Assignee: NICHEM FINE TECHNOLOGY CO., LTD, Hsinchu County (TW)

(*) Notice: Subject to any disclaimer, the term of this patent is extended or adjusted under 35 U.S.C. 154(b) by 135 days.

(21) Appl. No.: 15/227,989

(22) Filed: Aug. 4, 2016

(65) Prior Publication Data

US 2018/0040831 A1 Feb. 8, 2018

Related U.S. Application Data

(60) Provisional application No. 62/200,929, filed on Aug. 4, 2015.

(51) Int. Cl.
| | |
|---|---|
| *H01L 51/54* | (2006.01) |
| *C09K 11/06* | (2006.01) |
| *H01L 51/00* | (2006.01) |
| *C07D 403/14* | (2006.01) |
| *C07D 241/38* | (2006.01) |
| *C07D 409/14* | (2006.01) |
| *H01L 51/50* | (2006.01) |

(52) U.S. Cl.
CPC ........ *H01L 51/0072* (2013.01); *C07D 241/38* (2013.01); *C07D 403/14* (2013.01); *C07D 409/14* (2013.01); *H01L 51/0061* (2013.01); *H01L 51/0067* (2013.01); *H01L 51/0068* (2013.01); *H01L 51/5072* (2013.01); *H01L 51/5096* (2013.01)

(58) Field of Classification Search
CPC .. C07D 235/00; C07D 235/02; C07D 235/20; C07D 209/86; C07D 213/00; C07D 213/02; C07D 213/06; C07D 401/00; C07D 401/14; C07D 403/00; C07D 403/14; C07D 251/00; C07D 251/24; C07D 471/00; C07D 471/04; C07D 471/10; C07D 487/00; C07D 487/04; C07D 487/10; C07D 211/58; C07D 409/00; C07D 409/14; C07D 241/38; C07C 255/52; C07C 2603/32; C09K 11/025; C09K 11/06; C09D 2211/00; C09D 2211/10; C09D 2211/1007; C09D 2211/1011; C09D 2211/1014; C09D 2211/1029; C09D 2211/1044; Y02E 10/549; C07F 5/027; C07F 9/5329; H01L 51/0032; H01L 51/005; H01L 51/0051; H01L 51/0052; H01L 51/0056; H01L 51/0059; H01L 51/0061; H01L 51/0062; H01L 51/0067; H01L 51/0068; H01L 51/0071; H01L 51/0072; H01L 51/0073; H01L 51/0074; H01L 51/0095; H01L 51/44; H01L 51/424; H01L 51/50; H01L 51/5012; H01L 51/5016; H01L 51/5056; H01L 51/5072; H01L 51/5096
USPC ....... 428/690, 691, 917, 411.4, 336; 427/58, 427/66; 313/500–512; 257/40, 88–104, 257/E51.001–E51.052; 252/301.16–301.35
See application file for complete search history.

(56) References Cited

FOREIGN PATENT DOCUMENTS

KR      20110041730 A  *  4/2011

OTHER PUBLICATIONS

Machine translation of KR2011-0041730. (Year: 2011).*
Wei et al. J. Am. Chem. Soc. 2009, 131, 6698-6707. (Year: 2009).*
Supporting Information for Wei et al. J. Am. Chem. Soc. 2009, 131, 6698-6707. (Year: 2009).*
Supporting Information for Chen. et al. J. Am. Chem. Soc. 2006, 128, 10992-10993. (Year: 2006).*

* cited by examiner

*Primary Examiner* — Andrew K Bohaty
(74) *Attorney, Agent, or Firm* — The PL Law Group, PLLC

(57) ABSTRACT

An organic compound is disclosed. The organic compound includes a cis-stilbene segment, a bridge atom segment having a bridge atom with four bonds, and the bridge atom is connected to the cis-stilbene segment with two of the four bonds to form a 7-membered ring structure, and a quinoxaline segment connected to the cis-stilbene segment.

20 Claims, 2 Drawing Sheets

100

200

ORGANIC COMPOUND AND ELECTRONIC DEVICE USING SAME

CROSS-REFERENCE TO RELATED APPLICATION AND CLAIM OF PRIORITY

The application claims the benefit of the U.S. Provisional Patent Application No. 62/200,929, filed on Aug. 4, 2015, at the U.S. Intellectual Property Office, the disclosures of which are incorporated herein in their entirety by reference.

FIELD OF THE INVENTION

The present invention is related to an organic compound. In particular, the present invention is related to an organic compound for use in an electronic device.

BACKGROUND OF THE INVENTION

It is well known that the organic light emitting diode (OLED) was initially invented and proposed by the Eastman Kodak Company through a vacuum evaporation method. Tang and VanSlyke of the Kodak Company deposited an electron transport material such as Alq3 on a transparent indium tin oxide (abbreviated as ITO) glass formed with an organic layer of aromatic diamine thereon, and subsequently completed the fabrication of an organic electroluminescent (EL) device after a metal electrode was vapor-deposited onto the Alq3 layer. The organic EL device has become a new generation lighting device or display because of high brightness, fast response speed, light weight, compactness, true color, no difference in viewing angles, the lack of any LCD backlight plates, and low power consumption.

Recently, some interlayers such as an electron transport layer and a hole transport layer have been added between the cathode and the anode to increase the current efficiency and power efficiency of the OLEDs. For example, an OLED 100 shown as FIG. 1 includes a cathode 11, an electron injection layer 12, a light emitting layer 15, a hole transport layer 17, and an anode 18.

In the device function concept, the light emitted by the OLED 100 results from excitons produced by the recombination of electrons and holes in the light emitting layer 14. However, according to theoretical speculation, the ratio of the excitons with a singlet excited state and the excitons with a triplet excited state is 3:1. So, when a small molecular fluorescent material is used as the light-emitting layer 14 of the OLED 100, about 25% of the excitons are used to emit light, and the other 75% of the excitons in the triplet excited state are lost through a non-luminescence mechanism. For this reason, the general fluorescent material performs at a maximum quantum yield of 25%, a limit which amounts to an external quantum efficiency of 5% in the device.

Moreover, researchers further found that certain hole transport type materials can simultaneously perform electron confining, such as materials represented by the following Formulas 1' and 2'. Formula 1' represents the chemical structure of tris(4-carbazoyl-9-ylphenyl)amine, which is abbreviated TCTA. Formula 2 represents the chemical structure of N,N'-di(1-naphthyl)-N,N'-diphenyl-(1,1'-biphenyl)-4,4'-diamine, abbreviated NPB.

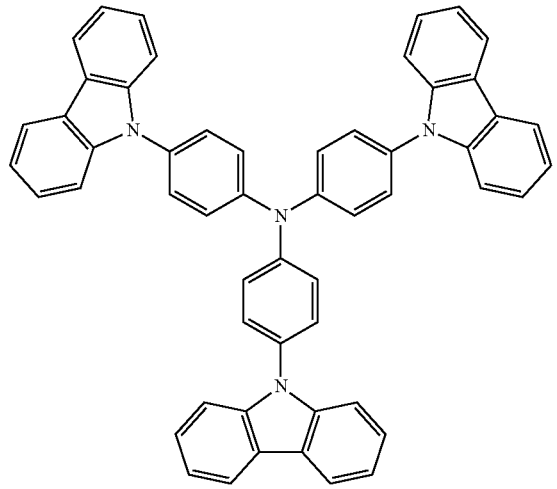

[Formula 1']

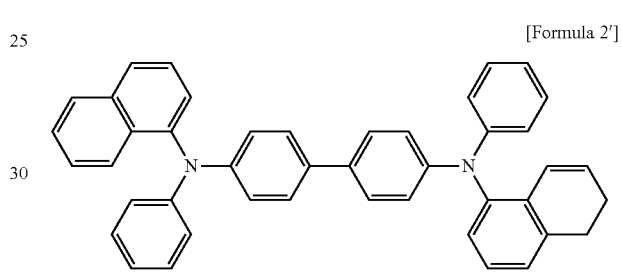

[Formula 2']

In addition, for effective blue-emitting performance in OLED applications, researchers have developed hole-transporting type, blue-emitters based on triarylamine dimer regimes, such as IDE-102, N-STIF-N developed in my laboratory, and spirobifluorene-based systems. These materials are represented by the following Formulas 3', 4', and 5'.

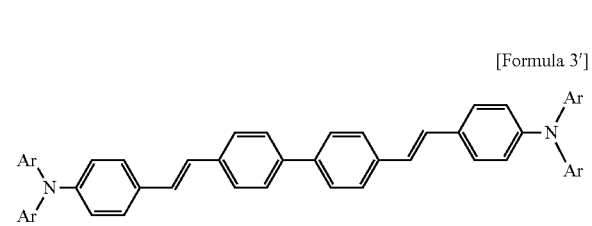

[Formula 3']

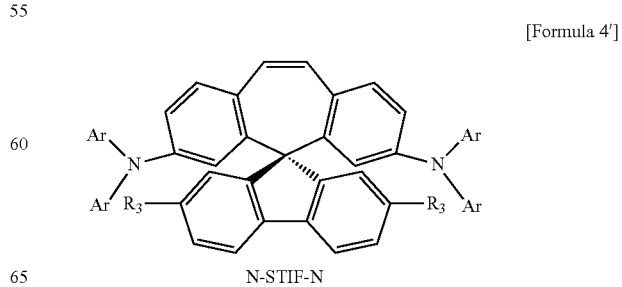

[Formula 4']

N-STIF-N

-continued

[Formula 5']

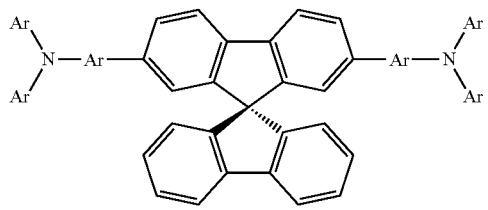

Recently, to effectively increase the light emitting performance of OLEDs, OLED manufactures and researchers have made great efforts to develop electron transport materials with hole blocking functionality, such as TmPyPb, TPBi, 3TPYMB, BmPyPb, and DPyPA represented by following Formula 6'-10', respectively. TmPyPb is the abbreviation of 3,3'-[5'-[3-(3-Pyridinyl)phenyl][1,1':3',1''-terphenyl]-3,3''-diyl]bispyridine, TPBi is the abbreviation of 1,3,5-Tris(1-phenyl-1H-benzimidazol-2-yl)benzene, 3TPYMB is the abbreviation of tris(2,4,6-triMethyl-3-(pyridin-3-yl)phenyl)borane, BmPyPb is the abbreviation of 1,3-bis(3,5-dipyrid-3-yl-phenyl)benzene, and DPyPA is the abbreviation of 9,10-bis(3-(pyridin-3-yl)phenyl) anthracene.

[Formula 6']

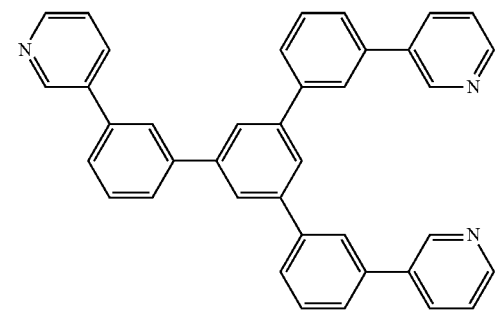

[Formula 7']

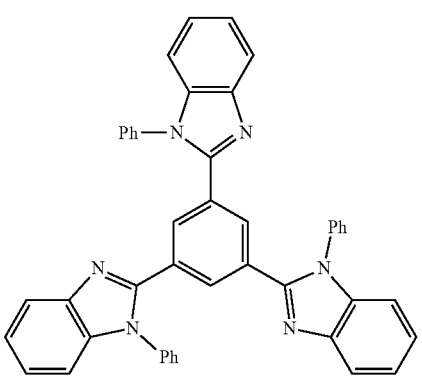

[Formula 8']

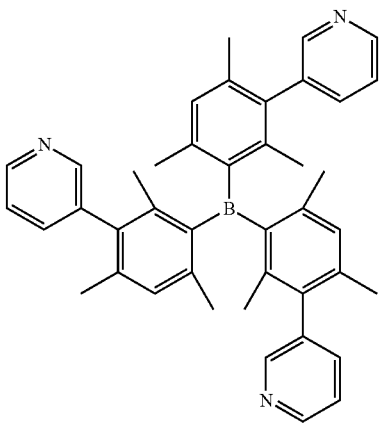

[Formula 9']

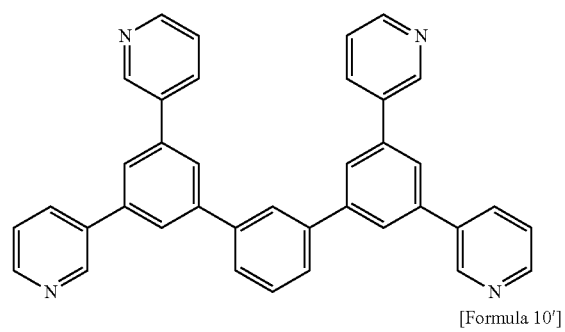

[Formula 10']

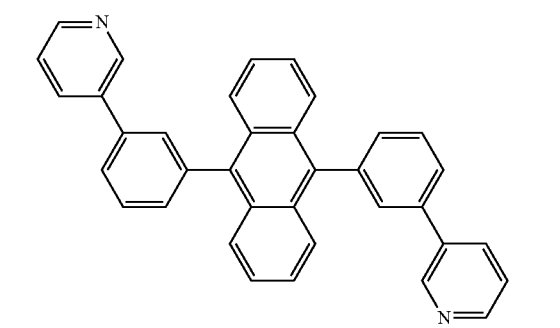

In spite of various electron transport materials with hole blocking functionality having been developed, the phosphorescence OLEDs that use these electron transport materials still cannot perform outstanding luminous efficiency with a long device lifetime. Accordingly, because the conventional or commercial electron transport materials with hole blocking functionality still have drawbacks, the inventor of the present application has made great efforts to make inventive research and eventually discovered a series of quinoxaline-fused, spirally configured cis-stilbene/fluorene hybrid materials bearing cyanoaryl and/or cyano-heteroaryl subunits as hole-blocking type electron-transporters and emitters for the OLED.

SUMMARY OF THE INVENTION

In accordance with one aspect of the present invention, an organic compound is disclosed. The organic compound includes a cis-stilbene segment, a bridge atom segment having a bridge atom with four bonds, and the bridge atom is connected to the cis-stilbene segment with two of the four bonds to form a 7-membered ring structure, and a quinozaline segment connected to the cis-stilbene segment.

In accordance with another aspect of the present invention, an electronic device made using a compound is disclosed. The electronic device includes a cis-stilbene segment, a bridge atom segment having a bridge atom with four bonds, and the bridge atom is connected to the cis-stilbene segment with two of the four bonds to form a 7-membered ring structure, and a quinozaline segment connected to the cis-stilbene segment.

The above objectives and advantages of the present invention will become more readily apparent to those ordinarily skilled in the art after reviewing the following detailed descriptions and accompanying drawings.

DETAILED DESCRIPTION OF THE PREFERRED EMBODIMENT

The present invention will now be described more specifically with reference to the following embodiments. It is to be noted that the following descriptions of preferred embodiments of this invention are presented herein for the purposes of illustration and description only; they are not intended to be exhaustive or to be limited to the precise form disclosed.

Figure 1:
FIG. 1 is an OLED structure according to prior art.
Figure 2:
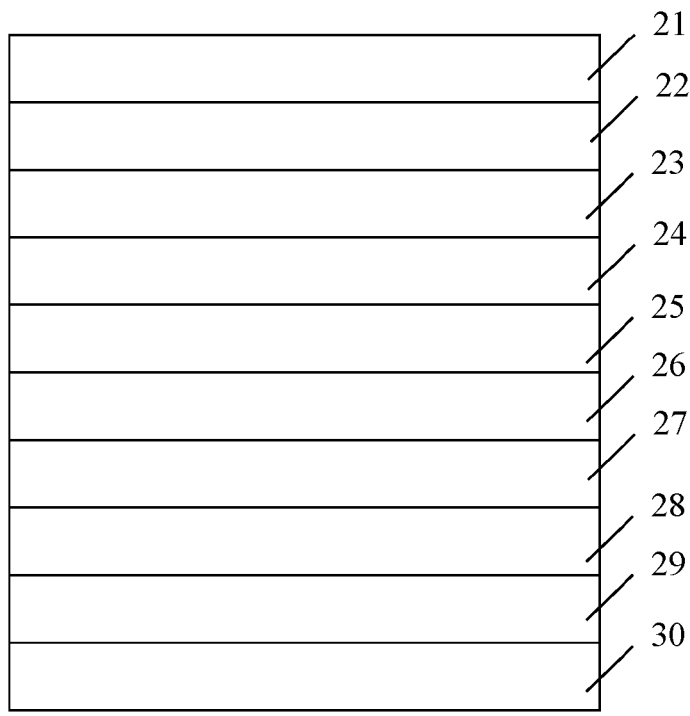
FIG. 2 is an OLED structure according to one embodiment of the present invention.
Figure 3:
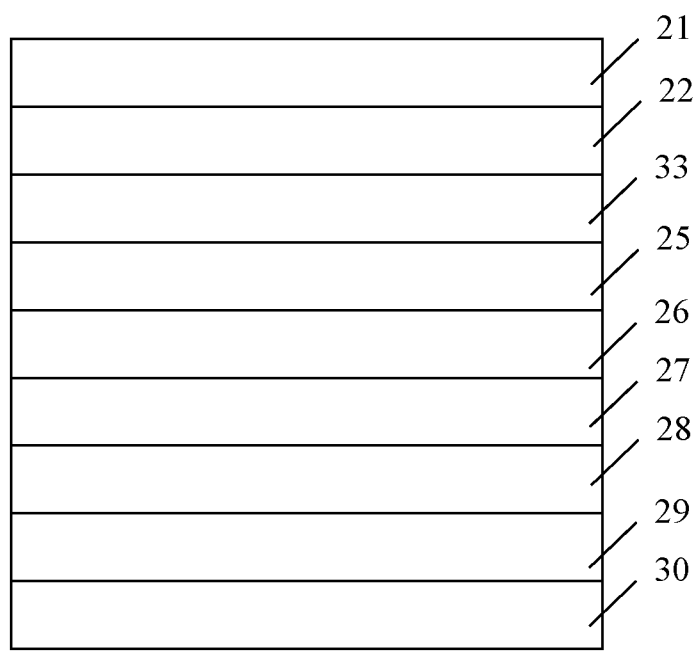
FIG. 3 is an OLED structure according to another embodiment of the present invention.

The present invention discloses an organic compound, which includes at least one of a series of quinoxaline-fused spirally configured cis-stilbene/fluorene compound and its derivatives. The compound includes a cis-stilbene segment, a bridge atom segment having a bridge atom with four bonds, and the bridge atom is connected to the cis-stilbene segment with two of the four bonds to form a 7-membered ring structure; and a quinoxaline segment connected to the cis-stilbene segment, and each of the other two of the four bonds is connected to one of methyl and phenyl. the compound or its derivatives can be applied in electronic devices such as fluorescent OLEDs as a material for a light emitting layer, an electron transport layer, a hole blocking layer, or a hole-blocking type electron transport layer. A structure of an OLED 200 of one embodiment of the present invention is shown in FIG. 2, which consecutively includes a cathode 21, an electron injecting layer 22, an electron transport layer 23, a hole blocking layer 24, a light emitting layer 25, an electron blocking layer 26, a hole transport layer 27, a hole injecting layer 28, an anode 29, and a substrate 30. When the electron transport layer 23 and the hole blocking layer 24 are formed as a single layer, the single layer is the hole-blocking type electron transport layer 3 made of the compound or its derivatives, as shown in an OLED 300 in FIG. 3.

Each of the electronic devices mentioned above can be applied to any device or apparatus having a display, such as one selected from a group consisting of an organic light emitting apparatus, a solar cell apparatus, an organic transistor, a detection apparatus, a computer monitor, a TV, a billboard, a light for interior or exterior illumination, a signaling light for interior or exterior illumination, a flexible display, a laser printer, a telephone, a cell phone, a remote control apparatus, a pad computer, a laptop computer, a digital camera, a camcorder, a viewfinder, a micro-display, a vehicle electronic apparatus, a large area wall display, a theater screen, a stadium screen, a signaling apparatus, a personal digital assistant (PDA), a laptop computer, an industrial computer, a point of sales (POS), a heads-up display, a fully transparent display, and a touch display.

According to one embodiment of the present invention, the quinoxaline segment in the organic compound is represented by Formula 1:

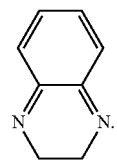

Formula 1

According to one embodiment of the present invention, the cis-stilbene segment in the organic compound is represented by Formula 2:

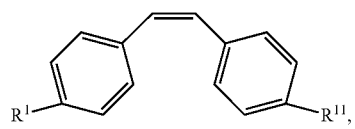

Formula 2 wherein each of $R^1$ and $R^{11}$ is one selected from a group consisting of H, halogen, —Ar, —CN, —NR$^4$R$^5$, —CF$_3$, —Ar—F, an aromatic amino group, Formulae 3a, 3b, 3c, 3d, 3e, 3f, 3g, 3h, 3j, 3k, 3l, 3m and 3n:

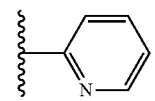

Formula 3a

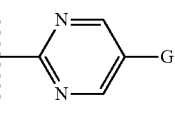

Formula 3b

Formula 3c

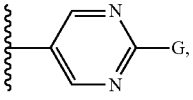

Formula 3d

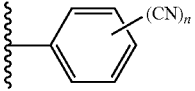

Formula 3e

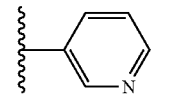

Formula 3f

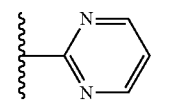

Formula 3g

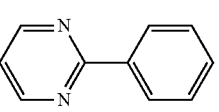

-continued

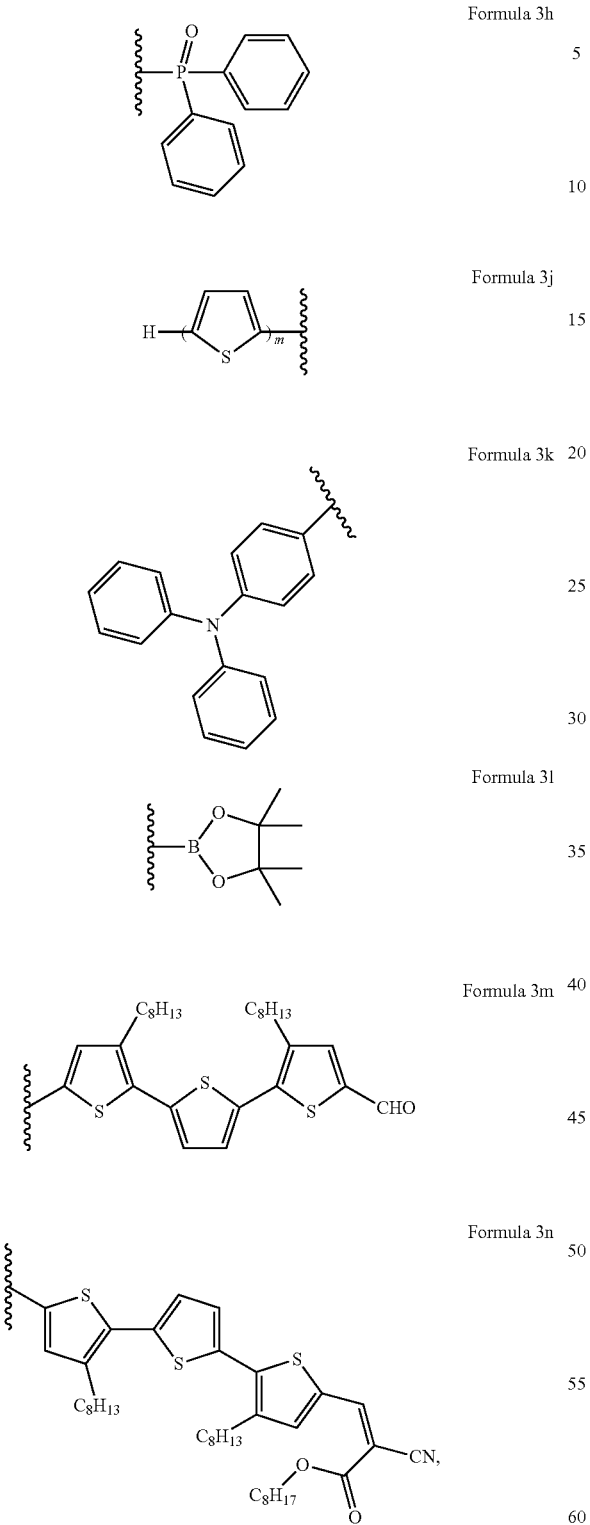

Formula 3h

Formula 3j

Formula 3k

Formula 3l

Formula 3m

Formula 3n

I either Ar and G is phenyl, the aromatic amino group is —NR⁴R⁵, wherein either of R⁴ and R⁵ is one selected from a group consisting of H and phenyl and naphthyl, n is an integer of 1-2, and m is an integer of 1-3, and —NR⁴R⁵ is represented by one of Formulae 3p, 3q and 3r:

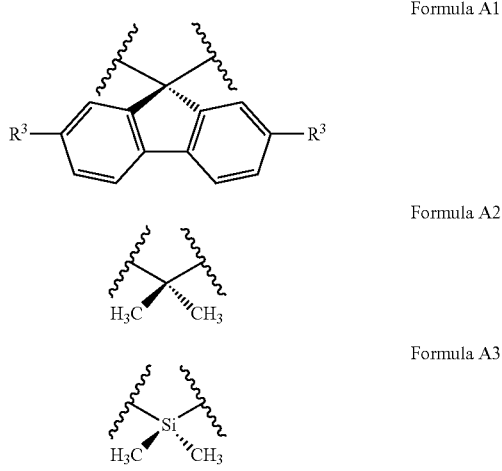

Formula 3p

Formula 3q

Formula 3r wherein X is one of H and a substituted or unsubstituted alkyl having 1 to 20 carbon atoms.

According to one embodiment of the present invention, wherein the bridge atom is one of carbon and silicon, the bridge atom segment connects to a methyl or a naphthyl by at least one of the other two bonds of the bridge atom. More specifically, the bridge atom segment is one selected from a group consisting of Formulae A1, A2, A3 and A4:

Formula A1

Formula A2

Formula A3

-continued

Formula A4

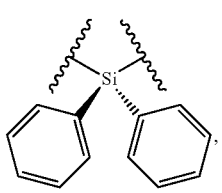

wherein $R^3$ is one selected from a group consisting of H, tert-butyl and naphthyl.

Embodiment 1

According to the first embodiment of the present invention, the organic compound is one of the quinoxaline-fused, spirally-configured cis-stilbene/fluorene compound and its derivatives, and is represented by the following Formula 4A:

Formula 4A

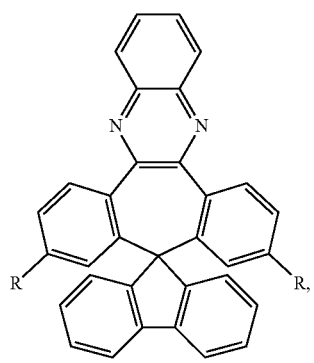

wherein R is the same as $R^1$ and $R^{11}$ previously described.

Embodiment 2

According to the second embodiment of the present invention, the organic compound is one of the quinoxaline-fused, spirally-configured cis-stilbene/fluorene compound and its derivatives, and is represented by the following Formula 4B:

Formula 4B

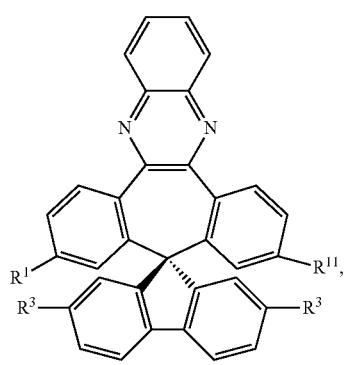

wherein $R^1$ and $R^{11}$ are the same as those previously described, and $R^3$ is one selected from a group consisting of H, tert-butyl and naphthyl.

Embodiment 3

According to the third embodiment of the present invention, the organic compound is one of the quinoxaline-fused, spirally-configured cis-stilbene/fluorene derivatives, and is represented by the following Formula 4C:

Formula 4C

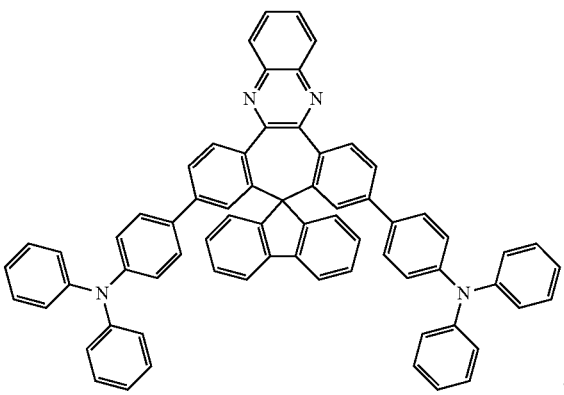 [SMILES: c1ccc(N(c2ccccc2)c2ccc(-c3ccc4c(c3)C3(c5ccccc5-c5ccccc53)c3cc(-c5ccc(N(c6ccccc6)c6ccccc6)cc5)ccc3-c3nc5ccccc5nc3-4)cc2)cc1]

The synthesis method of the organic compound represented by Formula 14 includes the following steps.

Formula 14

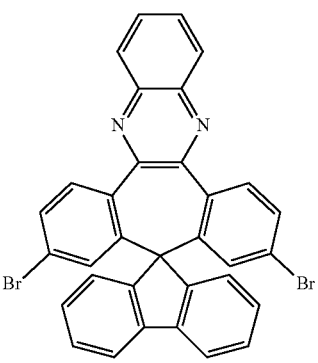

Step 1:

Consecutively add 5505.9 mg (equivalent to 10.7 mmol) of Compound 11 represented by Formula 11, 15 ml of acetic acid and 1.5 ml of concentrated hydrochloric acid into a reaction flask to form a solution. The color of the solution in the reaction flask will change to red. Install a reflux tube to the top of the reacting bottle. Put the reaction flask in an oil bath, at a temperature of about 120° C. After reacting for 30 minutes, the red color of the solution will fade and many precipitates will occur. The reaction flask is then lifted out of the oil bath and cooled down. Take off the reflux tube and use N-hexane to flush out the remaining silicon oil from the residue on the bottom. The residue on the bottom of the reaction flask is extracted using dichloromethane three times, each time with 50 ml, and water. The obtained organic extract solution is dried by adding magnesium sulfate, filtered, and then dried using rotary evaporation to withdraw the solvents to obtain a crude product. The crude product is purified by column chromatography using dichloromethane and water in a ratio of 1:3, and then further purified by recrystallization using dichloromethane and N-hexane, to obtain 4985.3 mg of solid Compound 12 represented by Formula 12, which is 3,7-dibromo-5,5-spirofluorenyl-5H-dibenzo[a,d]cycloheptene. Yield is 91%.

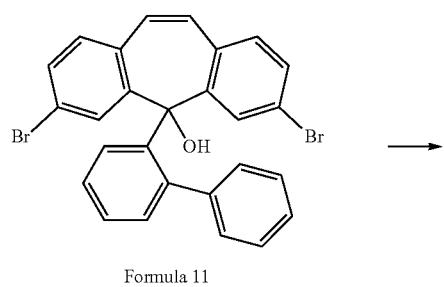

Formula 11

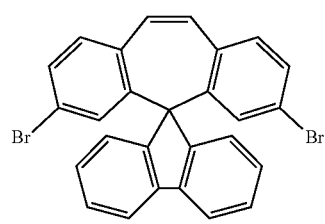

Formula 12

NMR data for Compound 12 are shown as follows: m.p. 283° C. (DSC); M.W.: 500.22; $^1$H NMR (400 MHz, CDCl$_3$) δ 7.90 (d, J=7.7, 2H), 7.76 (d, J=7.6, 2H), 7.42 (t, J=7.5, 2H), 7.32 (dd, J=8.2, 2.0, 2H), 7.29 (d, J=7.6, 2H), 7.20 (d, J=8.2, 2H), 6.98 (s, 2H), 6.90 (s, 2H); $^{13}$C NMR (100 MHz, CDCl$_3$) δ 151.53, 143.45, 138.86, 135.18, 133.54, 132.64, 131.91, 130.49, 128.59, 127.87, 126.66, 122.78, 120.59, 65.25; MS (FAB) 499.9 (M$^+$); TLC R$_f$ 0.35 (CH$_2$Cl$_2$/hexane, 1/5).

Step 2:

Add 2489.8 mg (5 mmol) of Compound 12, 2340.8 mg (6.5 mmol) of benzeneseleninic anhydride (BSA) and 20 ml of chlorobenzene to a reaction flask with a reflux tube thereon in an oil bath at a temperature of about 130° C. to react for 18 hours. Thin layer chromatography (TLC) is then used to confirm that no reactants exist. The reaction flask is lifted out of the oil bath and cooled down. Take off the reflux tube and use N-hexane to flush out the remaining silicon oil from the residue on the bottom. Rotary evaporation is used to evaporate the chlorobenzene from the residue. 20 ml of N-hexane are added to a suction funnel with 2 cm thick silicone gel and filters therein to dissolve a by-product diphenylselenide in the residue and filter the residue to obtain the solid filtrate, which is further flushed with N-hexane several times, each time with 20 ml. The solid filtrate is purified by recrystallization using dichloromethane and N-hexane to obtain 2164.5 mg of solid Compound 13, which is represented by Formula 13. Yield is 82%. The by-product, diphenylselenide, can be recycled at the same time.

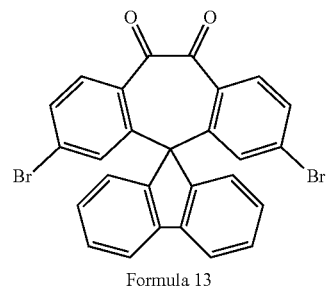

Formula 13

NMR data for Compound 13 are shown as follows: m.p. 257.1° C. (DSC); M.W.: 527.94; $^1$H NMR (400 MHz, CDCl$_3$) δ 7.86 (d, J=7.6, 2H), 7.72 (d, J=8.3, 2H), 7.49 (dd, J=8.3, 1.62, 2H), 7.46 (t, J=7.5, 2H), 7.22 (t, J=7.7, 2H), 7.29 (t, J=7.6, 2H), 7.66 (d, J=7.1, 2H), 6.72 (s, 2H); $^{13}$C NMR (100 MHz, CDCl$_3$) δ 197.10, 152.64, 144.45, 139.48, 133.34, 132.83, 131.77, 131.16, 129.31, 129.05, 128.87, 125.41, 121.21, 67.34; MS (FAB) 529.2 (M$^+$); TLC R$_f$ 0.3 (CH$_2$Cl$_2$/hexane, 1/3).

Step 3:

A 50 ml two-necked round-bottomed flask, as a reaction flask, with a stirrer therein, and equipped with a reflux tube is used. After the reaction flask is dried using a vacuum system, and then filled with nitrogen gas, 1060 mg (2 mmol) of Compound 13, 238 mg (2.2 mmol) of o-phenylenediamine and the catalyst p-toluenesulfonic acid dissolved in 20 ml of ethanol, are added to the reaction flask. Then the reflux device is turned on, and the reaction flask is placed in a preheated oil bath at a temperature of about 80° C. to react for 12 hours. After the reaction flask is cooled down, the saturated sodium bicarbonate solution is added in to quench the reaction. The residue on the bottom of the reaction flask is extracted using dichloromethane three times, each time with 20 ml. The obtained organic extract solution is dried by adding magnesium sulfate, filtered, and then dried using rotary evaporation to withdraw the solvents to obtain a crude product. The crude product is purified using column chromatography with dichloromethane and hexanes in a ratio of 1:2 to obtain 940 mg of Compound 14 represented by Formula 14. Yield is 78%.

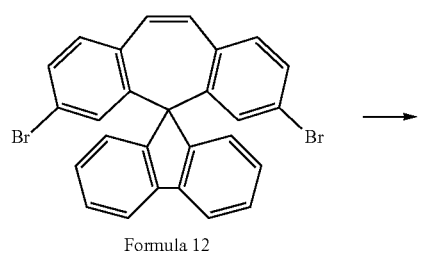

Formula 12

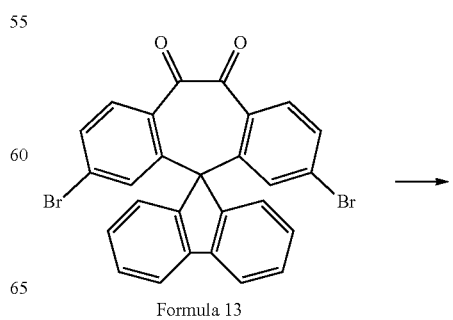

Formula 13

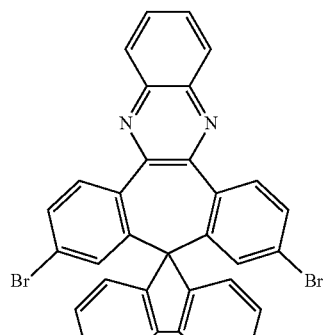

Formula 14

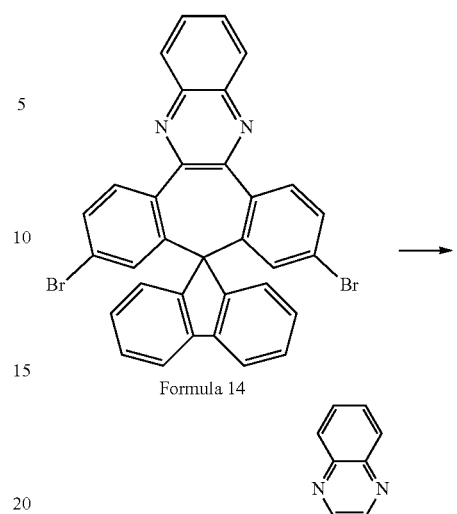

Formula 14

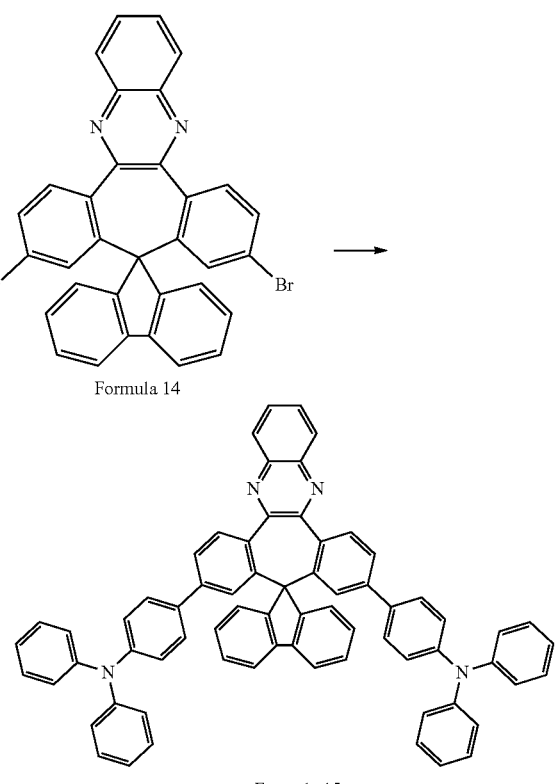

Formula 15

NMR data for Compound 14 are shown as follows: m.p. 298 □ (DSC); M.W.: 602.32; $^1$H NMR (400 MHz, CDCl$_3$) δ 8.27 (q, J=3.2, 2H), 8.25 (d, J=8.2, 2H), 7.90 (q, J=3.2, 2H), 7.77 (d, J=7.6, 2H), 7.58 (dd, J=8.2, 1.9, 2H), 7.36 (t, J=6.9, 2H), 7.33 (d, J=1.9, 2H), 7.07 (bs, 2H), 6.65 (bs, 2H); $^{13}$C NMR (100 MHz, CDCl$_3$) □ δ 151.9, 148.1, 147.0, 141.8, 140.1, 136.9, 134.8, 131.4, 131.1, 130.7, 129.5, 128.6, 127.5, 124.7, 120.8, 65.7; MS (ESI) 601.0 (M+H$^+$); TLC R$_f$ 0.40 (CH$_2$Cl$_2$/hexanes, 1/2); HR-MS calcd for C$_{33}$H$_{18}$Br$_2$N$_2$: 599.9837, found: 599.9816.

Step 4:

A 50 ml two-necked round-bottomed flask, as a reaction flask, with a stirrer therein, and equipped with a reflux tube is used. After the reaction flask is dried using a vacuum system, and then filled with nitrogen gas, 602 mg (1 mmol) of Compound 14 and 35 mg (0.03 mmol) of the catalyst triphenylphosphine palladium (Pd(PPh$_3$)$_4$) are added, then 20 ml of 1,2-dimethoxyethane is added using a syringe and mixed therewith for 10 minutes, 694 mg (2.4 mmol) of p-diphenylaminoboronic acid and 1 ml of 0.1 M sodium carbonate aqueous solution are added, and finally the reflux device is turned on to react for 12 hours. After the reaction flask is cooled down, oxygen is used to quench the reaction. The residue on the bottom of the reaction flask is extracted using dichloromethane three times, each time with 20 ml. The obtained organic extract solution is dried by adding magnesium sulfate, filtered, and then dried using rotary evaporation to withdraw the solvents to obtain a crude product. The crude product is purified using column chromatography with dichloromethane and hexanes in a ratio of 1:1 to obtain 847 mg of Compound 15, which is 3,7-bis(4-(N,N-diphenylamino)-phenyl)-5,5-spirofluorenyl-dibenzo-suberene[d]quinoxaline, represented by Formula 15. Yield is 91%.

NMR data for Compound 15 are shown as follows: T$_d$ 210° C. (TgA); T$_g$ 523° C. (DSC); M.W.: 931.13; $^1$H NMR (400 MHZ, CDCl$_3$) δ·8.44 (d, J=8.2, 2H), 8.31 (q, J=3.3, 2H), 7.87 (q, J=3.3, 2H), 7.72 (d, J=7.4, 2H), 7.67 (dd, J=8.1, 1.6, 8H), 7.48 (d, J=1.6, 2H), 7.30-7.23 (in, 16H), 7.09 (d, J=7.7, 8H), 7.03 (t, J=8.0, 10H); $^{13}$C NMR (100 MHz, CDCl$_3$) δ 152.9, 149.6, 147.6, 147.5, 146.1, 141.8, 141.2, 140.2, 136.4, 133.8, 133.7, 130.1, 129.5, 129.3, 128.1, 127.5, 127.1, 126.8, 125.8, 124.7, 123.4, 123.1, 120.5, 66.8; MS (ESI) 931.4 (M+H$^+$); TLC R$_f$ 0.45 (CH$_2$Cl$_2$/hexane, 1/1); HR-MS calcd for C$_{69}$H$_{46}$N$_4$: 930.3722, found: 930.3855; Anal. Calcd for C$_{69}$H$_{46}$N$_4$: C, 89.00, H, 4.98, N, 6.02. Found: C, 89.09, H, 4.98, N, 6.17.

Compound 14 can be further modified to obtain various quinoxaline-fused, spirally configured cis-stilbene/fluorene compounds such as Compounds 16-18 represented by Formulae 16-18. The synthesis method for the organic includes the following steps.

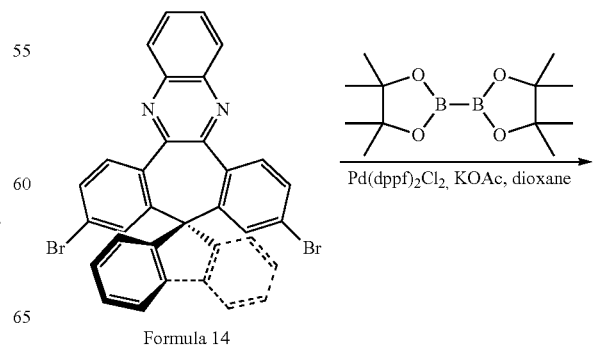

Formula 14

-continued

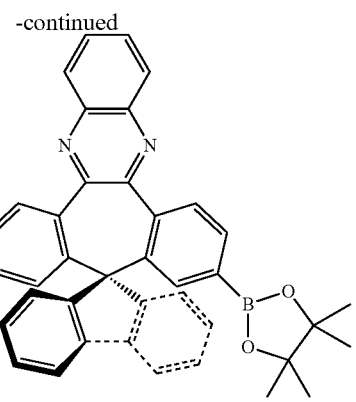

Formula 16

Step 5

A 50 ml two-necked round-bottomed flask, as a reaction flask, with a stirrer therein, and equipped with a reflux tube is used. After the reaction flask is dried using a vacuum system and is then filled with nitrogen gas, 602 mg (1 mmol) of Compound 14, 588 mg (2.2 mmol) of bis(pinacolato) diboron, 409 mg (6 mmol) of potassium acetate and 36 mg (0.05 mmol) of catalyst Pd(dppf)Cl$_2$ are subsequently added, then 20 ml of oxygen-free dioxone is added using a syringe, and the reaction flask is heated and refluxed to react for 18 hours. After the reaction flask is cooled down, oxygen is used to quench the reaction. The residue on the bottom of the reaction flask is extracted using dichloromethane three times, each time with 20 ml. The obtained organic extract solution is dried by adding magnesium sulfate, filtered with diatomite, and then dried using rotary evaporation to withdraw the solvents to obtain a crude product. The crude product is washed using methanol three times, each time with 20 ml, to obtain 408 mg (0.79 mmol) of white solid Compound 16 represented by Formula 16. Yield is 79%.

Step 6

A 25 ml two-necked round-bottomed flask, as a reaction flask, with a stirrer therein, and equipped with a reflux tube is used. 184 mg (0.5 mmol) of Compound 16, 321 mg (3 mmol) of sodium carbonate, 307 mg (1.1 mmol) of 5"-(4-bromo)-3,3"-di-n-hexyl-2,2':5',2"-terthiophene-5-carbaldehyde and 27 mg (0.03 mmol) of catalyst tetrakis(triphenylphosphine) palladium (Pd(PPh$_3$)$_4$) are subsequently added. After oxygen gas in the reaction flask is removed and it is filled with nitrogen gas, 10 ml of oxygen-free 1,2-dimethoxyethane and 1 ml of water are added using a syringe, and the reflux device is turned on to react for 18 hours. After the reaction ends and then the reaction flask is cooled down, oxygen is used to quench the reaction. The residue on the bottom of the reaction flask is extracted using dichloromethane three times, each time with 20 ml. The obtained organic extract solution is dried by adding magnesium sulfate, filtered, and then dried using rotary evaporation to obtain a crude product. The crude product is purified and concentrated using column chromatography with dichloromethane and hexanes in a ratio of 1:2 to obtain 528 mg (0.39 mmol) of Compound 17 represented by Formula 17. Yield is 79%.

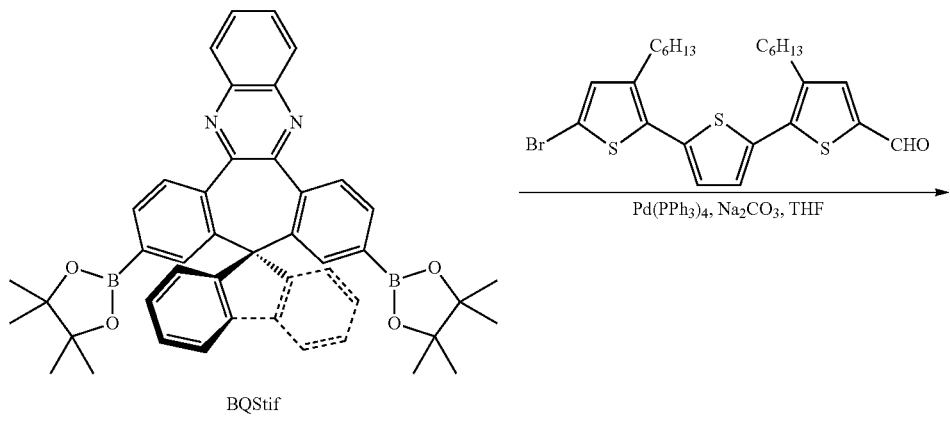

BQStif

Formula 16

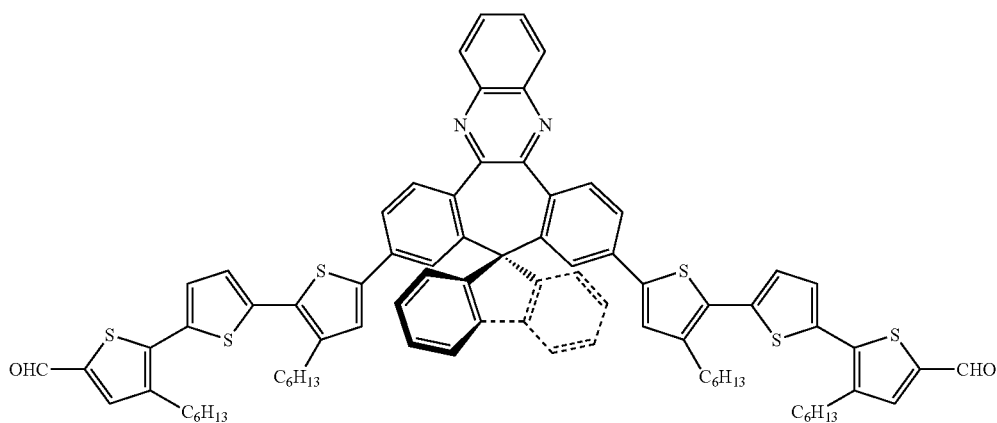

Formula 17

17

Step 7

A 50 ml two-necked round-bottomed flask, as a reaction flask, with a stirrer therein is used. 64 mg (0.05 mmol) of Compound 17, 6 mg (0.23 mmol) of octylcyanoacetate, 10 ml of anhydrous chloroform as solvent are subsequently added, and then two drops of triethylamine are added. The above mixture is reacted at room temperature for 18 hours, and then is extracted using dichloromethane and water. The obtained organic extract solution is dried by adding magnesium sulfate, filtered, and then dried using rotary evaporation to obtain a crude product. The crude product is purified using column chromatography with dichloromethane and hexanes in a ratio of 1:1 to obtain 62 mg (0.04 mmol) of dark red solid Compound 18 represented by Formula 18. Yield is 76%.

18

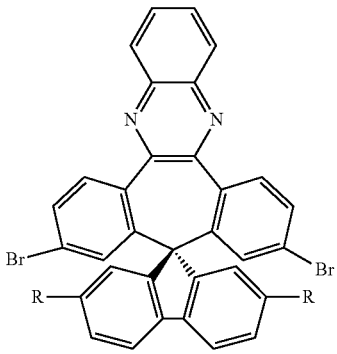

Formula 19

Furthermore, various exemplary embodiments for the quinoxaline-fused, spirally configured cis-stilbene/fluorene hybrid materials of the present invention can be fabricated

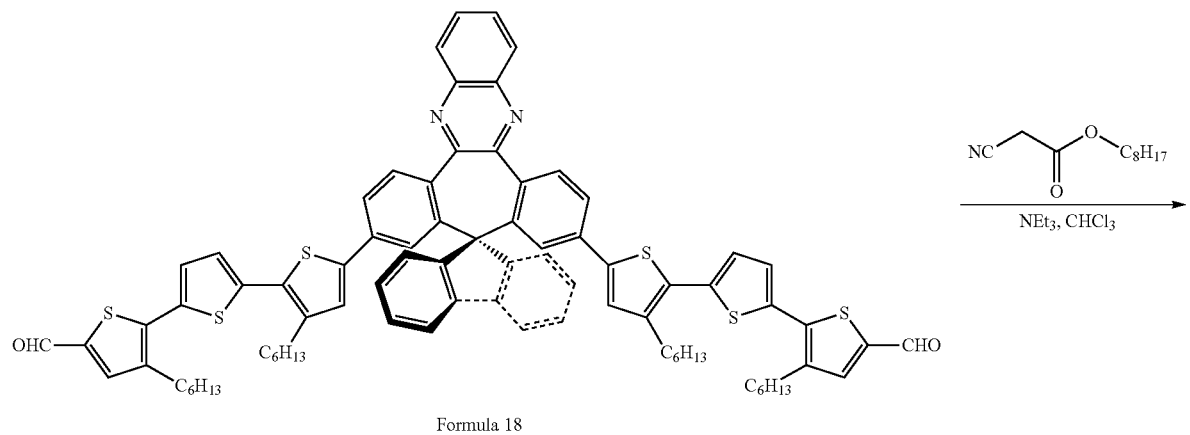

Formula 18

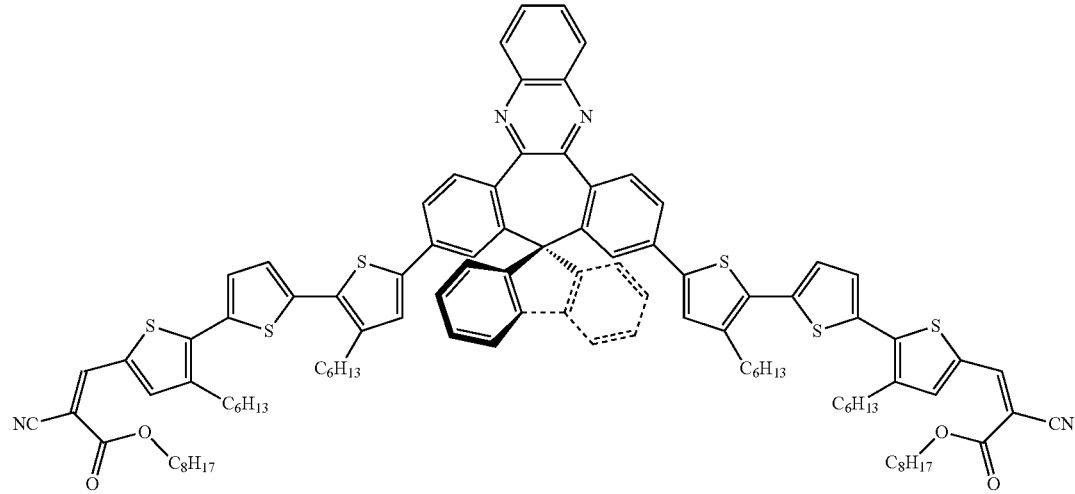

Formula 17

Using a similar method to the above, the skilled person in the art can obtain the key intermediate product of clear crystalline materials represented by Formula 19, wherein R is one selected from a group consisting of H, tert-butyl and naphthyl.

using certain chemical reaction methods to the key intermediate product of the clear crystalline materials represented by Formula 19, such as Suzuki coupling reactions. Therefore, the exemplary Compounds 20-23 of these quinoxaline-fused, spirally configured cis-stilbene/fluorene hybrid materials are represented by following Formulae 20-23:

Formula 20

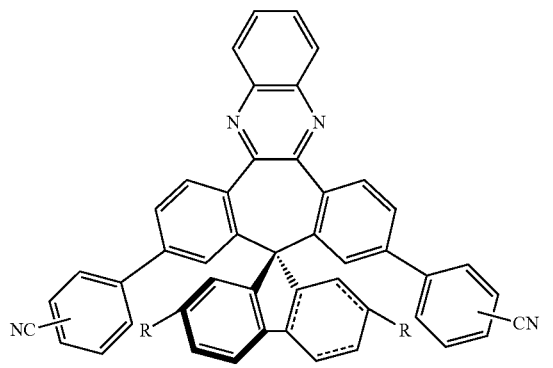

Formula 21

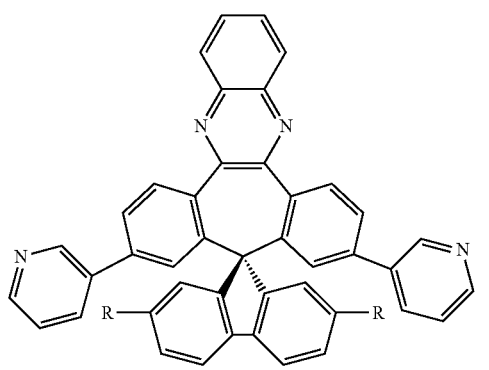

Formula 22

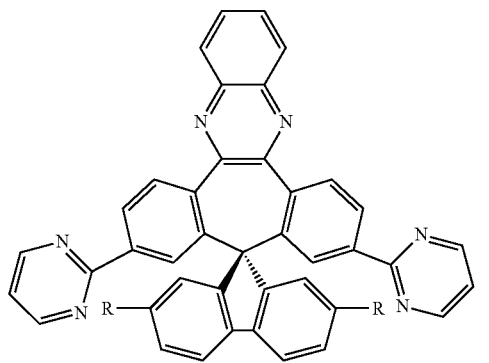

Formula 23

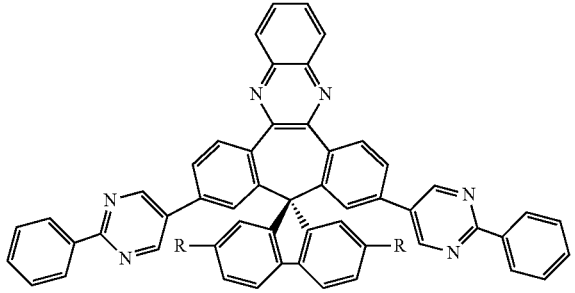

wherein R is one selected from a group consisting of H, tert-butyl and naphthyl.

A mixture of 7.7 mmol of Compound 19 represented by Formula 19, 16.9 mmol of (2- or 3-cyanophenyl)boronic acid or other type of boronic acids, 985 mg (0.09 mmol) of Pd(PPh3)4 and 3.3 g (30.8 mmol) of sodium carbonate are added in 100 ml of toluene, 10 ml of ethanol, and 10 ml of distilled water is heated to 85° C. for 24 hours under argon atmosphere. The mixture was then extracted with dichloromethane 3 times, each time with 35 mL. The extracts are dried using about 2 g of anhydrous MgSO4 and concentrated by rotary evaporation. The crude product is purified by column chromatography on silica gel with dichloromethane and hexanes in a ratio of 2:1 as an eluent to obtain a white solid compound, which is one of Compounds 20-23 represented by Formulae 20-23. Yield is 61-75%.

NMR data for the compound of Formula 20 are shown as follows. $T_m$ 357° C. M.W.: 646.75; $^1$H NMR (400 MHz, CDCl$_3$) δ 8.52 (d, J=8.0, 2H), 8.34-8.32 (m, 2H), 7.95-7.91 (m, 2H), 7.77 (d, J=7.8 Hz, 2H), 7.71-7.63 (m, 4H), 7.47-7.43 (m, 6H), 7.10 (bs, 2H), 6.80 (bs, 2H); $^{13}$C NMR (100 MHz, CDCl$_3$) δ 152.25, 149.01, 146.20, 144.60, 141.89, 139.80, 138.22, 134.15, 132.63, 130.74, 129.57, 127.60, 127.46, 126.52, 120.89, 118.70, 111.29; TLC $R_f$ 0.32 (CH$_2$Cl$_2$/hexanes, 2/1); HRMS calcd for C$_{47}$H$_{26}$N$_4$: 646.2157, found: 646.2149.

NMR data for the compound of Formula 22 are shown as follows. $T_m$ 383° C. (DSC); M.W.: 600.69; $^1$H NM (400 MHz, CDCl$_3$) δ 8.61 (d, J=4.8, 4H), 8.54 (d, J=8.0, 2H), 8.37-8.35 (m, 2H), 8.25 (dd, J=8.0, 1.7, 2H), 8.17 (d, J=1.6, 2H), 8.07 (d, J=7.8, 2H), 7.77 (d, J=7.6, 2H), 7.50 (d, J=8.0, 2H), 7.41 (td, J=7.5, 1.0, 2H), 7.11 (bs, 2H), 6.85 (t, J=4.8, 2H); $^{13}$C NMR (100 MHz, CDCl$_3$) δ 164.3, 157.0, 152.6, 152.4, 149.5, 142.2, 139.1, 138.6, 137.5, 133.9, 132.7, 129.2, 128.0, 127.5, 127.0, 126.9, 120.4, 118.7, 66.3; TLC $R_f$ 0.25 (CH$_2$Cl$_2$/hexanes, 3/1); HR-MS (ESI) Anal. Calcd for C$_{41}$H$_{24}$N$_6$: 600.2062, found: 600.2066.

The data for the glass transition temperature ($T_g$), decomposition temperature ($T_d$), the longest peak wavelength value of the absorption spectrum ($\lambda_{max}$), and the longest peak wavelength value of the photoluminescence spectrum (PL_$\lambda_{max}$) of Compounds 20-23 were measured and are recorded in the following Table 1. In Table 1, Φ represents a phenyl group, C represents carbon, N represents nitrogen, QS represents the quinoxaline-fused spirally configured cis-stilbene/fluorene structure, Py represents pyradinyl, and each of Pm and Pm' represents pyrimidinyl.

TABLE 1

| Group n = 1 | $T_g$ (° C.) | $T_d$ (° C.) | $\lambda_{max}$ (nm) | PL $\lambda_{max}$ (nm) |
|---|---|---|---|---|
| Compound 20 (CNΦQSΦCN) | 209 | 428 | 365 | 407 |
| Compound 21 (PyQSPy) | 172 | 421 | 367 | 405 |
| Compound 22 (PmQSPm) | 169 | 419 | 369 | 403 |
| Compound 23 (ΦPm'QSPm' Φ) | 175 | 417 | 370 | 415 |

From Table 1, it is easy to see that these quinoxaline-fused, spirally-configured cis-stilbene/fluorene derivatives proposed in the present invention have glass transition temperatures ($T_g$) that range from 165° C. to 175° C. and decomposition temperatures ($T_d$) that range from 413° C. to 421° C. This means that these quinoxaline-fused, spirally-configured cis-stilbene/fluorene derivatives possess excellent thermal stability, and will not easily decompose under high voltage or high current density operating conditions.

Moreover, the oxidation potential and the redox potential of Compounds 20-23 of these quinoxaline-fused, spirally-configured cis-stilbene/fluorene derivatives can be measured using cyclic voltammetry (CV). In Table 2, $E_{1/2ox}$ and $E_{1/2red}$ of the quinoxaline-fused, spirally-configured cis-stilbene/fluorene derivatives are recorded.

TABLE 2

| Group | $E_{1/2}^{ox}$ (V) | $E_{1/2}^{red}$ (V) |
| --- | --- | --- |
| Compound 20 (CNΦQSΦCN) | 1.25 | −2.04 |
| Compound 21 (PyQSPy) | 1.28 | −1.97 |
| Compound 22 (PmQSPm) | 1.30 | −1.91 |
| Compound 23 (ΦPm'QSPm'Φ) | 1.29 | −1.93 |

From Table 2, a skilled person in the art of OLED materials can see that these quinoxaline-fused, spirally-configured cis-stilbene/fluorene derivatives proposed in the present invention have oxidation potentials that range from 1.25 V to 1.3 V and redox potentials that range from −1.91 V to −2.04 V.

A process for manufacturing an OLED device according to the present invention is described as follows. An aluminum substrate is cleaned by detergent. The cleaned aluminum substrate is loaded into a evaporation machine in a vacuum environment of about $7 \times 10^{-6}$ torr to coat the cleaned aluminum substrate with various organic materials and metals listed in the following Table 3. The evaporation machine is purged with nitrogen and the coated substrate is removed for evaluation. Alternatively, an ITO glass can also be used to manufacture the OLED device. The ITO glass is cleaned and put into an evaporation machine. The various organic materials and metals can be deposited onto the ITO glass in a reverse sequence, to obtain the OLED device.

In order to prove that these proposed quinoxaline-fused, spirally-configured cis-stilbene/fluorene hybrid materials can indeed be applied in OLEDs as a hole-blocking type electron transport layer and/or an emitting layer, a plurality of OLED devices for control groups and experimental groups were designed and manufactured, wherein the constituting layers for the OLED devices are shown in the following Table 3.

TABLE 3

| Device Group | Substrate | bottom electrode | electron transport layer | hole blocking layer | light emitting layer | hole transport layer | hole injection layer | top electrode |
| --- | --- | --- | --- | --- | --- | --- | --- | --- |
| Experiment 1 | Al | LiF | Compound 20 (CNΦQSΦCN) | Compound 20 (ΦQSΦ) | green phosphorescent compound | TAPC | HATCN | ITO |
| Experiment 2 | Al | LiF | Compound 21 (PyQSPy) | Compound 21 (PyQSPy) | green phosphorescent compound | TAPC | HATCN | ITO |
| Experiment 3 | Al | LiF | Compound 22 (PmQSPm) | Compound 22 (PmQSPm) | green phosphorescent compound | TAPC | HATCN | ITO |
| Experiment 4 | Al | LiF | Compound 23 (ΦPm'QSPm'Φ) | Compound 23 (ΦPm'QSPm'Φ) | Green phosphorescent compound | TAPC | HATCN | ITO |
| Control 1A | Al | LiF | BmPyPb | BmPyPb | green phosphorescent compound | TAPC | HATCN | ITO |
| Control 1B | Al | LiF | DPyPA | DPyPA | green phosphorescent compound | TAPC | HATCN | ITO |
| Control 1C | Al | LiF | TPBi | TPBi | green phosphorescent compound | TAPC | HATCN | ITO |
| Experiment 5 | Al | LiF | Compound 20 (CNΦQSΦCN) | Compound 20 (CNΦQΦCN) | green phosphorescent compound | NPB/TAPC | HATCN | ITO |
| Experiment 6 | Al | LiF | Compound 21 (PyQSPy) | Compound 21 (PyQSPy) | green phosphorescent compound | NPB/TAPC | HATCN | ITO |
| Control 2 | Al | LiF | BmPyPb | BmPyPb | green phosphorescent compound | NPB/TAPC | HATCN | ITO |
| Control 3 | Al | LiF | ET01 | ET01 | green phosphorescent compound | NPB/TAPC | HATCN | ITO |

In Table 3, BmPyPb is the abbreviation of 1,3-bis(3,5-dipyrid-3-yl-phenyl)benzene, DPyPA is the abbreviation of 9,10-bis(3-(pyridin-3-yl)phenyl)anthracene, TPBi is the abbreviation of 1,3,5-Tris(1-phenyl-1H-benzimidazol-2-yl)benzene, and NPB is the abbreviation of N,N'-di(1-naphthyl)-N,N'-diphenyl-(1,1'-biphenyl)-4,4'-diamine. In addition, ET01 is represented by Formula 24, TAPC is the abbreviation of 4,4'-cyclohexylidene bis[N,N-bis(4-methylphenyl)benzenamine], HATCN is the abbreviation of 1,4,5,8,9,11-hexaazatriphenylene hexacarbonitrile, and the green phosphorescent compound 11-(4,6-diphenyl-1,3,5-triazin-2-yl)-12-phenyl-11,12-dihydroindolo[2,3-a]carbazole is represented by Formula 25.

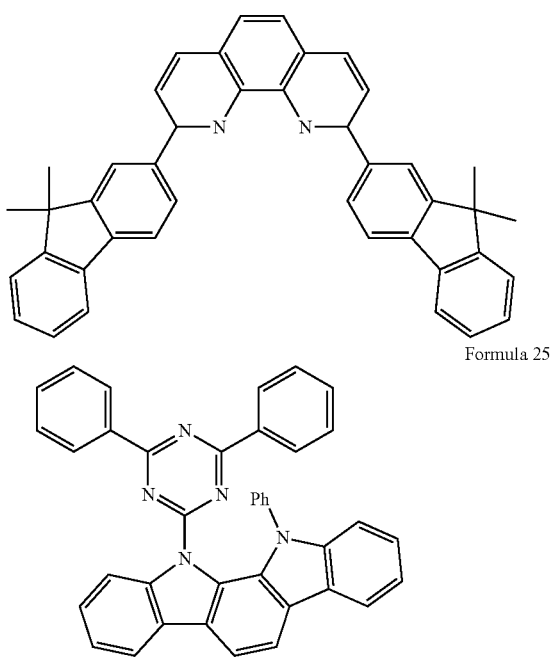

Formula 24

Formula 25

The materials of TPBi, DPyPA, BmPyPb and ET01 recorded in Table 3 are also used as the OLED device's electron transport layers. The turn-on voltage ($V_{on}$), the external quantum efficiency ($\eta_{ext}$), the current efficiency ($\eta_c$), the power efficiency ($\eta_p$), and the maximum luminance ($L_{max}$) of the OLED devices were measured and are recorded in Table 4.

TABLE 4

| Device Group | $\lambda_{max}$ (nm) | $V_{on}$ (V) | $\eta_{ext}$ (%) | $\eta_c$ (cd/A) | $\eta_p$ (lm/w) | $L_{max}$ (cd/m$^2$) |
| --- | --- | --- | --- | --- | --- | --- |
| Experiment 1 | 516 | 2.1 | 17.6 | 63.2 | 64.7 | 139,200 |
| Experiment 2 | 516 | 2.2 | 16.6 | 57.1 | 65.1 | 145,320 |
| Experiment 3 | 516 | 2.3 | 12.8 | 51.6 | 62.5 | 124,800 |
| Experiment 4 | 516 | 2.3 | 11.4 | 45.4 | 60.4 | 100,860 |
| Control 1A | 516 | 2.5 | 6.3 | 22.8 | 18.0 | 142,100 |
| Control 1B | 516 | 3.0 | 10.2 | 37.8 | 24.0 | 40,700 |
| Control 1C | 516 | 3.0 | 6.9 | 24.7 | 22.0 | 37,640 |
| Experiment 5 | 516 | 4.7 | 12.9 | 45.1 | 26.5 | 76,930 |
| Experiment 6 | 516 | 4.7 | 13.6 | 48.3 | 26.8 | 73,200 |
| Control 2 | 516 | 4.5 | 10.8 | 36.8 | 25.7 | 42,150 |
| Control 3 | 516 | 5.5 | 7.84 | 27.6 | 15.8 | 17,700 |

With reference to the measured data for the green phosphorescent OLED devices in Table 4, one can find that the OLED devices using a single hole transport layer from Experiments 1-4 show excellent $\eta_{ext}$, $\eta_c$, $\eta_p$, and $L_{max}$, and are much superior to the OLED devices with a single hole transport layer of Control 1A, Control 1B and Control 1C. Among them, Experiment 1 (CNΦQSΦCN) and 2 (Py-QSPy) show the best results, where the $\eta_{ext}$ are in a range of 15.0-15.7%, $\eta_c$ are in a range of 54.5-55.8 cd/A, $\eta_p$ are in a range of 64.7-70.2 lm/w, and $L_{max}$ are in a range of 139,200-145,320 cd/m$^2$.

In addition, the measured data also reveal that the OLED devices using a single hole transport layer in Experiment 5 and Experiment 6 show excellent $\eta_{ext}$, $\eta_c$, $\eta_p$, and $L_{max}$, which are superior to the OLED devices using complex (i.e., double) hole transport layer of Control 2 and Control 3. Moreover, the commercial OLED device using a complex hole transport layer (or called double hole transport layer) in Experiment 6 (PyQSPy) also shows excellent $\eta_{ext}$, $\eta_c$, $\eta_p$, and $L_{max}$, which is superior to the OLED devices using a complex hole transport layer of Control 2 and Control 3.

Furthermore, device life time evaluation tests for the green phosphorescent OLEDs were also completed based on a starting luminance of 10,000 cd/cm$^2$. The life time evaluation test results reveal that the decay half lifetimes ($LT_{50}$) of the green phosphorescent OLED in Experiment 5 and 6 are 15,500 and 16,840 hours. In addition, the decay half lifetime ($LT_{50}$) for the green phosphorescent OLEDs of Control 1A and Control 3 were respectively measured as 1,000 hours and 13,500 hours. Moreover, after replacing the BmPyPb in the green phosphorescent OLEDs of Control 1A with the TmPyPb, the green phosphorescent OLEDs having the TmPyPb material was measured with the $LT_{50}$ of only 210 hours.

Through the above descriptions, the quinoxaline-fused, spirally-configured cis-stilbene/fluorene compound and its derivatives for OLEDs proposed in the present invention have been completely and clearly introduced. In summary, the present invention includes the advantages of:

(1) The quinoxaline-fused, spirally-configured cis-stilbene/fluorene hybrid materials are quinoxaline-fused, spirally-configured cis-stilbene/fluorene compound and its derivatives with cayanoaryl and cyanoheteroaryl substituents with glass transition temperatures that range from 165° C. to 175° C., and decomposition temperatures that range from 413° C. to 421° C.

(2) In addition, a variety of experimental data prove that these quinoxaline-fused, spirally-configured cis-stilbene/fluorene compound and its derivatives can indeed be used as a hole-blocking type electron-transporter for OLEDs. Moreover, the experimental data also reveal that OLEDs using these quinoxaline-fused, spirally-configured cis-stilbene/fluorene compound and its derivatives used as the hole-blocking type electron-transporter show excellent external quantum efficiency ($\eta_{ext}$), current efficiency ($\eta_c$), power efficiency ($\eta_p$), maximum luminance ($L_{max}$), and device lifetime performance, which are all better than conventional or commercial OLEDs.

While the invention has been described in terms of what is presently considered to be the most practical and preferred embodiments, it is to be understood that the invention needs not be limited to the disclosed embodiments. On the contrary, it is intended to cover various modifications and similar arrangements included within the spirit and scope of the appended claims, which are to be accorded with the broadest interpretation so as to encompass all such modifications and similar structures.

What is claimed is:
1. An organic compound comprising:
a cis-stilbene segment;
a bridge atom segment having a bridge atom with four bonds, and the bridge atom is connected to the cis-stilbene segment with two of the four bonds to form a 7-membered ring structure; and
a quinoxaline segment connected to the cis-stilbene segment, wherein the quinoxaline segment is unsubstituted at C5 and C8 positions thereof.

2. An organic compound according to claim 1, wherein either of the other two of the four bonds is connected to one of methyl and phenyl.

3. An organic compound according to claim 2, wherein the bridge atom is, one of carbon and silicon, and the bridge atom segment is one selected from a group consisting of Formulae A1, A2, A3 and A4:

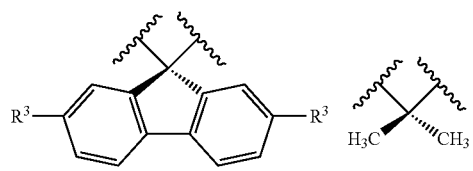

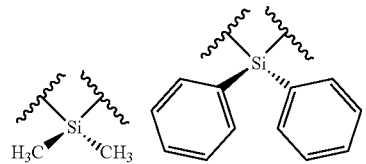

Formula A1 Formula A2 Formula A3 Formula A4,
wherein $R^3$ is one selected from a group consisting of H, tert-butyl and naphthyl.

4. An organic compound according to claim 1, wherein the compound has at least one of a glass transition temperature (Tg) ranging from 165° C. to 175° C., a decomposition temperature ($T_d$) ranging from 413° C. to 421° C., an oxidation potential ranging from 1.25V to 1.30 V, and a reduction potential ranging from −1.91 V to −2.04 V.

5. An organic compound according to claim 1, wherein the compound is represented by Formula 4:

Formula 4

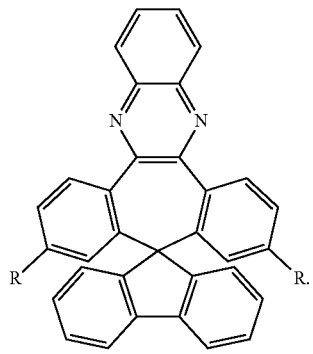

wherein each of R is one selected from the group consisting of H, halogen, —Ar, —CN, —NR$^4$R$^5$, —CF$_3$, —Ar—F, an aromatic amino group, Formulae 3a, 3b, 3c, 3d, 3e, 3f, 3g, 3h, 3j, 3k, 3l, 3m and 3n:

Formula 3a
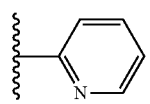

Formula 3b
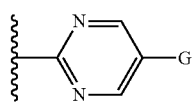

Formula 3c
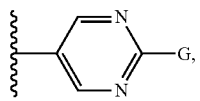

Formula 3d
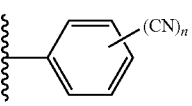

Formula 3e
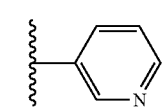

Formula 3f
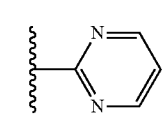

Formula 3g
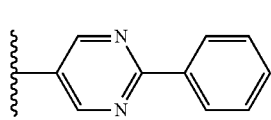

Formula 3h
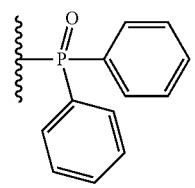

Formula 3j
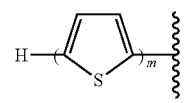

Formula 3k
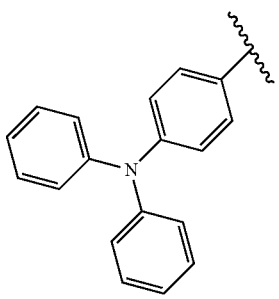

Formula 3l
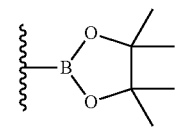

Formula 3m
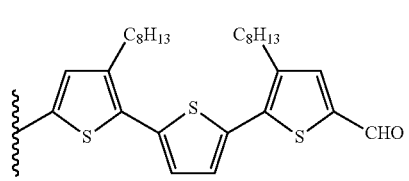

-continued

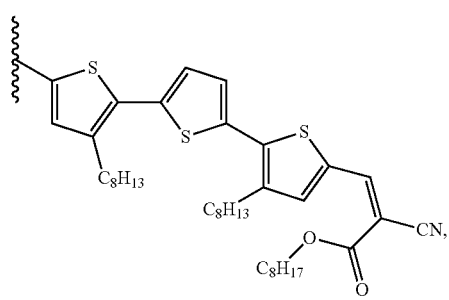

Formula 3n wherein the halogen is one selected from the group consisting of F, Cl, Br and I, either of Ar and G is phenyl, the aromatic amino group is —NR$^4$R$^5$, wherein either of R$^4$ and R$^5$ is one selected from the group consisting of H, phenyl and naphthyl, n=an integer of 1-2, and m is an integer of 1-3.

6. An organic compound according to claim 1, wherein the compound is applied to at least one material selected from a group consisting of an electron transport layer, a light-emitting layer and a combination thereof in an organic light emitting diode (OLED).

7. An electronic device made using a compound, the compound comprising:
a cis-stilbene segment;
a bridge atom segment having a bridge atom with four bonds, wherein the bridge atom is one of carbon and silicon, and the bridge atom is connected to the cis-stilbene segment with two of the four bonds to form a 7-membered ring structure; and,
wherein the quinozaline segment is unsubstituted at C5 and C8 positions thereof
a quinoxaline segment connected to the cis-stilbene segment.

8. An electronic device according to claim 7, wherein the quinoxaline segment is represented by Formula 1:

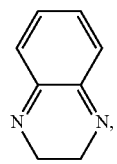

Formula 1 and the cis-stilbene segment is a 4,4'-substituted cis-stilbene segment represented by Formula 2:

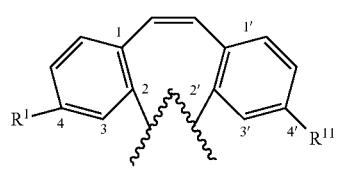

Formula 2 wherein either of R$^1$ and R$^{11}$ is one selected from a group consisting of H, halogen, —Ar, —CN, —NR$^4$R$^5$, —CF$_3$, —Ar—F, an aromatic amino group, Formulae 3a, 3b, 3c, 3d, 3e, 3f, 3g, 3h, 3j, 3k, 3l, 3m and 3n:

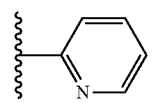

Formula 3a

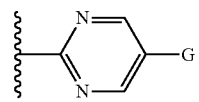

Formula 3b

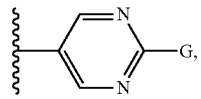

Formula 3c

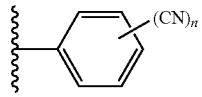

Formula 3d

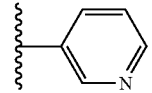

Formula 3e

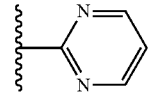

Formula 3f

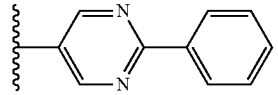

Formula 3g

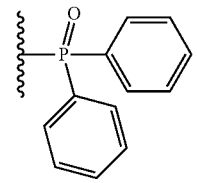

Formula 3h

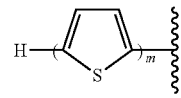

Formula 3j

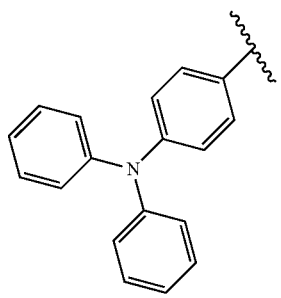

Formula 3k

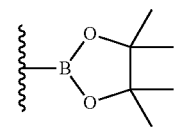

Formula 3l

-continued

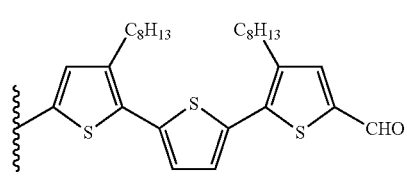
Formula 3m

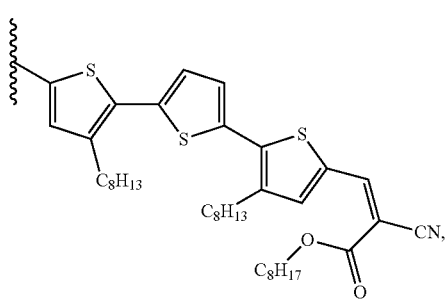
Formula 3n wherein the halogen is one selected from a group consisting of F, Cl, Br and I, either of Ar and G is phenyl, the aromatic amino group is —NR$^4$R$^5$, wherein either of R$^4$ and R$^5$ is one selected from a group consisting of H, phenyl and naphthyl, n=an integer of 1-2, and m is an integer of 1-3.

9. An electronic device according to claim 8, wherein —NR$^4$R$^5$ is represented by one of Formulae 3p, 3q and 3r:

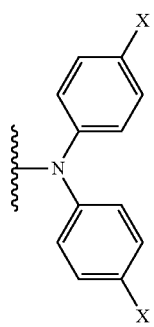
Formula 3p

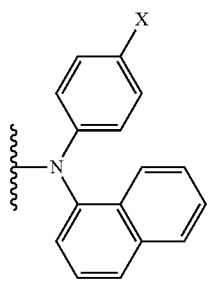
Formula 3q

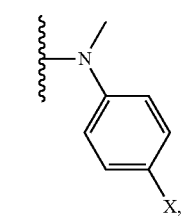
Formula 3r wherein X is one of H and a substituted or unsubstituted alkyl having 1 to 20 carbon atoms.

10. An electronic device according to claim 7, wherein either of the other two of the four bonds is connected to one of methyl and phenyl.

11. An electronic device according to claim 10, wherein the bridge atom is one of carbon and silicon, and the bridge atom segment is one selected from a group consisting of Formulae A1, A2, A3 and A4:

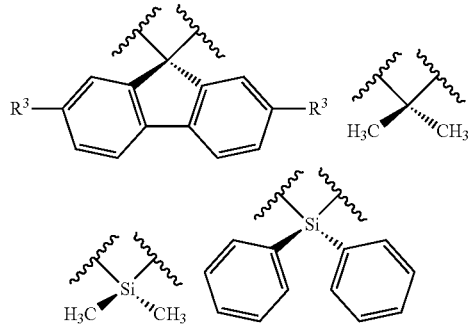

Formula A1 Formula A2 Formula A3 Formula A4,
wherein R$^3$ is one selected from a group consisting of H, tert-butt and naphthyl.

12. An electronic device according to claim 7, comprising:
a first electrode;
a second electrode disposed opposite to the first electrode; and
an organic layer disposed between the first electrode and the second electrode,
wherein the organic layer is, made using the compound.

13. An electronic device according to claim 12, wherein the electronic device is an organic light emitting device, the first electrode is a cathode, the second electrode is an anode, and the organic layer includes one selected from a group consisting of an electron transport layer, a hole blocking layer, a light emitting layer, and a combination thereof, when the organic layer is a combination of the electron transport layer and the hole blocking layer, the organic layer is formed as a first single layer.

14. An electronic device according to claim 13, further comprising at least one selected from a group consisting of a hole transport layer disposed between the light emitting layer and the anode, an electron blocking layer disposed between the hole transport and the light emitting layer, and a hole injecting layer between the anode and the hole transport layer, and when the organic layer is a combination of the electron transport layer, the hole blocking layer and the light emitting layer, the organic layer is formed as a second single layer.

15. An electronic device according to claim 7, wherein the electronic device is applied to one selected from a group consisting of an organic light emitting apparatus, a solar cell, apparatus, an organic transistor, a detection apparatus, a computer monitor, a TV, a billboard, a light for interior or exterior illumination, a signaling light for interior or exterior illumination, a flexible display, a laser printer, a telephone, a cell phone, a remote control apparatus, a pad computer, a laptop computer, a digital camera, a camcorder, a viewfinder, a micro-display, a vehicle electronic apparatus, a large area wall display, a theater screen, a stadium screen, a signaling apparatus, a personal digital assistant (PDA), a laptop computer, an industrial computer, a point of sales (POS), a heads-up display, a fully transparent display, and a touch display.

16. An organic compound according to claim 1, wherein the quinoxaline segment is represented by Formula 1:

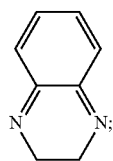

[Formula 1]

and the cis-stilbene segment is a 4,4'-substituted cis-stilbene segment represented by Formula 2:

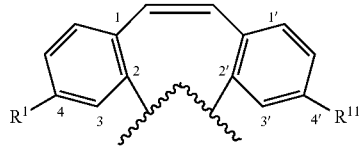

[Formula 2]

wherein either of $R^1$ and $R^{11}$ is one selected from a group consisting of H, halogen, —Ar, —CN, —NR$^4$R$^5$, —CF$_3$, —Ar—F, an aromatic amino group, Formulae 3a, 3b, 3c, 3d, 3e, 3f, 3g, 3h, 3j, 3k, 3l, 3m and 3n:

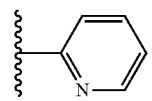

Formula 3a

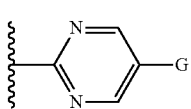

Formula 3b

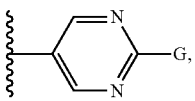

Formula 3c

Formula 3d

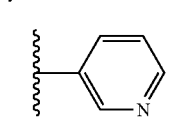

Formula 3e

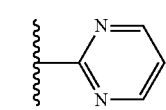

Formula 3f

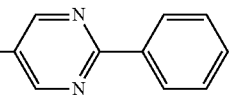

Formula 3g

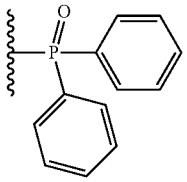

Formula 3h

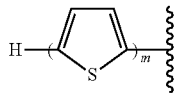

Formula 3j

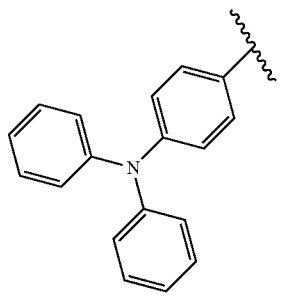

Formula 3k

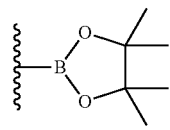

Formula 3l

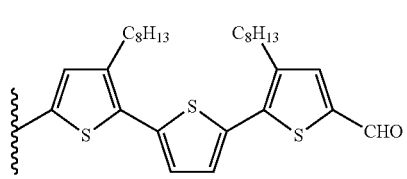

Formula 3m

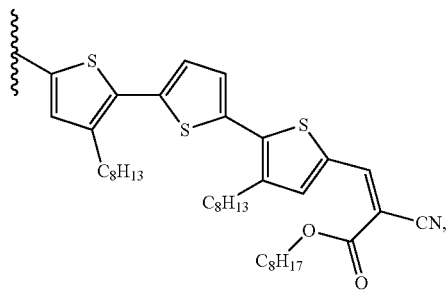

Formula 3n wherein the halogen is one selected from a group consisting of F, Cl, Br and I, either of Ar and G is phenyl, the aromatic amino group is —NR$^4$R$^5$, wherein either of R$^4$ and R$^5$ is one selected from a group consisting of H, phenyl and naphthyl, n is an integer of 1-2, and m is an integer of 1-3.

17. An organic compound according to claim 16, wherein —NR$^4$R$^5$ is represented by one of Formulae 3p, 3q and 3r:

Formula 3p

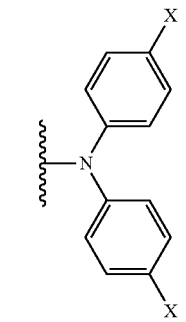

Formula 3q

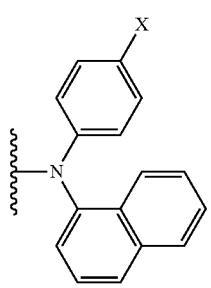

Formula 3r

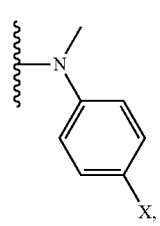

wherein X is one of H and a substituted or unsubstituted alkyl having 1 to 20 carbon atoms.

18. A method for manufacturing an organic compound represented by Formula 4, comprising:

Formula 4

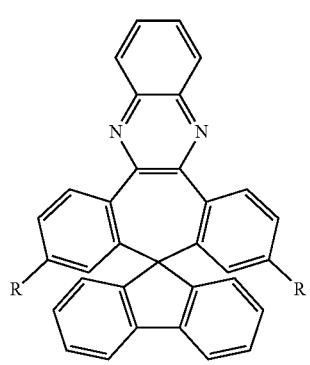

reacting a compound represented by Formula 11 with an acid to form a compound represented by Formula 12;

Formula 11

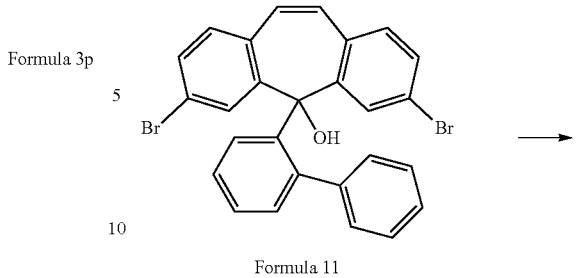

Formula 12

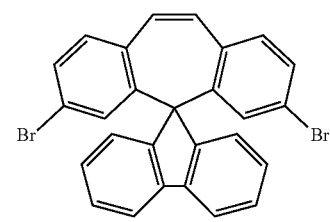

reacting the compound represented by Formula 12 with an anhydride to form a compound represented by Formula 13; and Formula 12

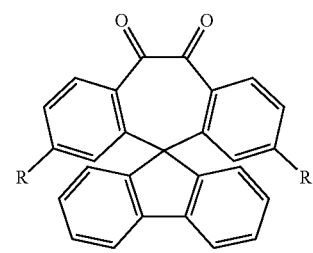

Formula 13

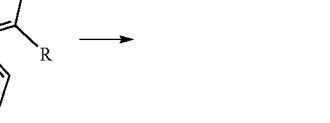

reacting the compound represented by Formula 13 with an o-phenylenediamine to form a compound represented by Formula 4, Formula 13

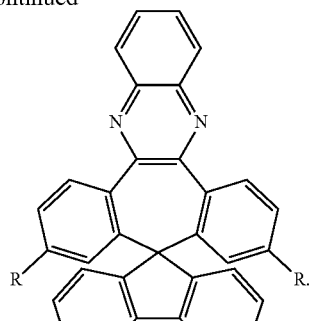

Formula 4 wherein R is one selected from a group consisting of H, halogen, —Ar, —CN, —NR⁴R⁵, —CF₃, —Ar—F, an aromatic amino group, Formulae 3a, 3b, 3c, 3d, 3e, 3f, 3g, 3h, 3j, 3k, 3l, 3m and 3n:

[Formulae 3a through 3j structures shown]

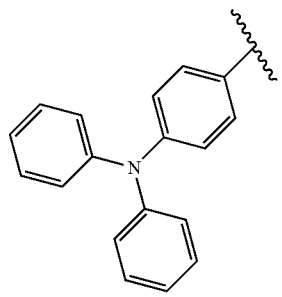

Formula 3k

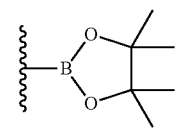

Formula 3l

[Formulae 3m and 3n structures shown]

wherein the halogen is one selected from a group consisting of F, Cl, Br and I, either of Ar and G is phenyl, the aromatic amino group is —NR⁴R⁵, wherein either of R⁴ and R⁵ is one selected from a group consisting of H and phenyl and naphthyl, n is an integer of 1-2, and m is an integer of 1-3.

19. A method according to claim 18, wherein when R is a diphenylamino phenyl, the compound represented by Formula 4 is a compound represented by Formula 15:

Formula 15
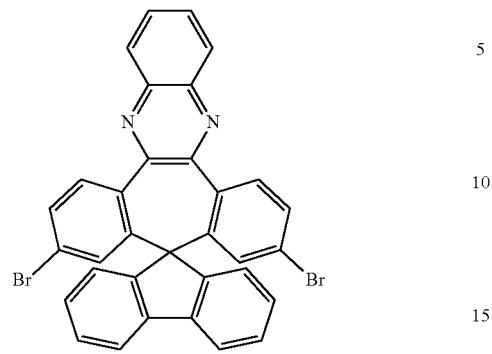
Formula 14
the method further comprising reacting the compound represented by Formula 14 with a p-diphenylamino phenyl boronic acid to obtain the compound represented by Formula 15.
20. A method according to claim 18, wherein the acid includes acetic acid and hydrochloric acid, and the anhydride is benzene selenic anhydride.
* * * * *